(12) United States Patent
Pare (10) Patent No.: US 12,075,860 B1
(45) Date of Patent: Sep. 3, 2024

(54) HIGH-PERFORMING LIQUID-COOLED APPAREL

(71) Applicant: Oceanit Laboratories, Inc., Honolulu, HI (US)

(72) Inventor: Raviraj Pare, Kailua, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 459 days.

(21) Appl. No.: 17/146,392

(22) Filed: Jan. 11, 2021

Related U.S. Application Data (60) Provisional application No. 62/959,800, filed on Jan. 10, 2020.

(51) Int. Cl.
*A41D 13/005* (2006.01)
*A41D 31/18* (2019.01)
(Continued)

(52) U.S. Cl.
CPC ......... *A41D 13/0053* (2013.01); *A41D 31/18* (2019.02); *A61F 7/0053* (2013.01);
(Continued)

(58) Field of Classification Search
CPC ..... A41D 13/0053; A61F 7/0053; A61F 7/02; F25D 3/005; F25D 2400/26
See application file for complete search history.

(56) References Cited

U.S. PATENT DOCUMENTS

| 7,089,753 B2 * | 8/2006 | Hoeks | F28F 9/26 62/235.1 |
| 9,301,557 B1 * | 4/2016 | Santos | B32B 5/02 |

(Continued)

FOREIGN PATENT DOCUMENTS

CN       203324460 U   * 12/2013

OTHER PUBLICATIONS

Murphy et al. (ICES2019175) "Advance Liquid Cooling and Ventilation Garment Using Thermally Conductive Tubing" (Year: 2019).*

(Continued)

*Primary Examiner* — Elizabeth J Martin
*Assistant Examiner* — Samba Nmn Gaye
(74) *Attorney, Agent, or Firm* — Fresh IP PLC; Clifford D. Hyra; Aubrey Y. Chen (57) ABSTRACT

Devices, systems, and methods for cooling and/or thermoregulation are disclosed, including thermoregulatory apparel. Such thermoregulatory apparel includes a cooling vest for human users to reduce their body temperature and/or to keep their body temperature below a certain value. The cooling vest may include a plurality of tubing arranged within the four-way stretch fabric used for the vest. Coolant flows through this tubing, which is arranged so that it contacts a user's skin while the user is wearing the vest. The composition and arrangement of the tubing can be matched with the type of fabric so that both the tubing and the fabric stretch in similar ways, ensuring that the tubing stays in contact with the user's skin. Also disclosed is a cartridge with a phase change material that is configured to refresh or recharge the cooling ability of the coolant when the coolant is passed through the phase change material.

28 Claims, 6 Drawing Sheets

(51) Int. Cl.
    *A61F 7/00*         (2006.01)
    *A61F 7/02*         (2006.01)
    *F25D 3/00*         (2006.01)

(52) U.S. Cl.
    CPC ............... *A61F 7/02* (2013.01); *F25D 3/005* (2013.01); *A41D 2300/20* (2013.01); *F25D 2400/26* (2013.01)

(56) References Cited

U.S. PATENT DOCUMENTS

| | | | |
|---|---|---|---|
| 2004/0079517 A1* | 4/2004 | Bueley | A41D 13/0053 165/138 |
| 2005/0139351 A1* | 6/2005 | Chambers | F28F 21/00 62/259.3 |
| 2006/0191063 A1* | 8/2006 | Elkins | A62B 17/005 2/458 |
| 2008/0184734 A1* | 8/2008 | Verma | F25B 9/008 62/515 |
| 2008/0188789 A1* | 8/2008 | Galavotti | A61M 37/00 524/568 |
| 2009/0264969 A1* | 10/2009 | Gammons | A61F 7/02 607/104 |
| 2018/0070659 A1* | 3/2018 | Xu | A41D 13/0053 |
| 2018/0120873 A1* | 5/2018 | Radermacher | G05D 23/1927 |
| 2020/0281284 A1* | 9/2020 | McAllister | A41D 13/0053 |

OTHER PUBLICATIONS

Translated_Zhang (Year: 2013).*

* cited by examiner

Cartridge
Recharging station

FIG. 6

HIGH-PERFORMING LIQUID-COOLED APPAREL

CROSS-REFERENCE TO RELATED APPLICATIONS

This application claims the benefit of U.S. Provisional Application No. 62/959,800, filed Jan. 10, 2020, which is incorporated by reference herein in its entirety.

The invention described herein was made with U.S. government ("Government") support under (1) Contract No. W911QY-17-C-0031, awarded by the U.S. Army and the Army Soldier Systems Center), and (2) Contract No. N00014-19-9-0017, awarded by the Office of Naval Research. As a result, the Government has certain rights in this invention.

FIELD OF THE INVENTION

The application relates generally to devices, systems, and methods for cooling and/or thermoregulation. In particular, the invention relates to thermoregulatory apparel wearable by humans and/or animals.

BACKGROUND

Wearable apparel that can help thermoregulate the user by, for example, providing heating and/or cooling is desirable, and even necessary, for a wide range of functions and use scenarios. For instance, soldiers depend on effective thermoregulatory apparel in order to keep them comfortable while performing physically and/or mentally demanding tasks.

Currently-available thermoregulatory apparel, however, is often only suitable for a narrow range of potential uses. Such apparel often fails to heat and/or cool efficiently, and is further bulky or heavy to wear. The various challenges with currently-available thermoregulatory apparel will be described in more detail with respect to the non-limiting example of cooling apparel, and, in particular, portable cooling vests.

Portable cooling vests must include portable systems, including, for instance, vapor compression systems, to circulate coolant through the vest. These systems must be carried by the user, such as, for example, in a backpack, which makes them expensive to produce and maintain, as well as impractical for long periods of use and/or for physically demanding tasks. Additionally, a user cannot control the amount and duration of cooling because such systems are not amenable to modification by the user.

Additionally, cooling vests often lack sufficient flexibility or stretch in order to adequately accommodate a user's movements, thereby limiting the effectiveness and potential use applications of such apparel. Many cooling vests are too rigid and constricting to enable the user to perform tasks that require a wide range of body movements and/or agility. Certain cooling vests attempt to address this issue by making the garment looser, but looser garments sacrifice the effective cooling.

Given the foregoing, there exists a significant need for wearable apparel that can provide adequate thermoregulation and, in particular, a need for wearable apparel that can provide adequate cooling for the user.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In certain embodiments, the disclosed embodiments may include one or more of the features described herein.

In general, the present invention is directed to devices, systems, and methods for cooling and/or thermoregulation. In particular, the invention relates to thermoregulatory apparel wearable by humans and/or animals.

The present invention in its various embodiments is directed to wearable apparel that is able to thermoregulate the user, such as, for example, by heating or cooling the user. In one or more embodiments of the invention, the apparel is a cooling vest comprising a plurality of tubing incorporated into the fabric of the vest. This tubing provides the ability to cool the user while stretching to accommodate the user's movements.

One of skill in the art will recognize that existing thermoregulatory apparel, including existing cooling apparel, is of limited use due to inflexibility, rigidity, and/or inability to provide adequate heating and/or cooling. Flexibility, in particular, is extremely important to allow for different users' needs. However, existing apparel does not optimize different factors such as the amount of cooling, the duration of cooling, the weight of the cooling system, and the flexibility of the apparel. The present invention therefore enables a balance between effective thermoregulation in a piece of wearable apparel, while maintaining suitable flexibility that accommodates a range of movements and use scenarios.

These and further and other objects and features of the invention are apparent in the disclosure, which includes the above and ongoing written specification, as well as the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art.

FIG. 1, and specifically

FIG. 2, and specifically

DETAILED DESCRIPTION

The present invention is more fully described below with reference to the accompanying figures. The following description is exemplary in that several embodiments are described (e.g., by use of the terms "preferably," "for example," or "in one embodiment"); however, such should not be viewed as limiting or as setting forth the only embodiments of the present invention, as the invention encompasses other embodiments not specifically recited in this description, including alternatives, modifications, and equivalents within the spirit and scope of the invention. Further, the use of the terms "invention," "present invention," "embodiment," and similar terms throughout the description are used broadly and not intended to mean that the invention requires, or is limited to, any particular aspect being described or that such description is the only manner in which the invention may be made or used. Additionally, the invention may be described in the context of specific applications; however, the invention may be used in a variety of applications not specifically described.

The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted. Further, the description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. Purely as a non-limiting example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an," and "the" are intended to include the plural forms as well, unless the context clearly indicates otherwise. It should also be noted that, in some alternative implementations, the functions and/or acts noted may occur out of the order as represented in at least one of the several figures. Purely as a non-limiting example, two figures shown in succession may in fact be executed substantially concurrently or may sometimes be executed in the reverse order, depending upon the functionality and/or acts described or depicted.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments, whether these features, elements and/or steps are included or are to be performed in any particular embodiment.

Generally, the present invention is directed towards devices, systems, and methods for cooling and/or thermoregulation. In particular, the invention relates to thermoregulatory apparel wearable by humans and/or animals.

In the context of this application, tubing that is "in contact" with a user or wearer's skin/body is arranged such that heat may be exchanged between the tubing and the skin by conduction. The tubing may or may not be in direct contact with the skin and, in some embodiments, may have one or more layers of material between the tubing and the skin.

Embodiments of the present invention comprise a cooling vest wearable by human users to cool down their body temperature and/or to keep their body temperature below a certain value. The cooling vest, in accordance with one or more embodiments of the instant invention, comprises a plurality of tubing, though which coolant flows, arranged within the fabric used for the vest. This fabric has a 4-way stretch, which is a term, familiar to one of skill in the art, for a fabric that is capable of stretching both crosswise and lengthwise. Non-limiting examples of such 4-way stretch fabrics include spandex and elastane. One of skill in the art will recognize that 4-way stretch fabrics have been incorporated into a variety of clothing, including, but not limited to, sports apparel, such as swimwear and leotards, general athletic wear, loungewear, and the like. This stretch of the fabric enables increased contact of the tubes with the skin, reducing any airgaps that may be present.

Figure 1A:
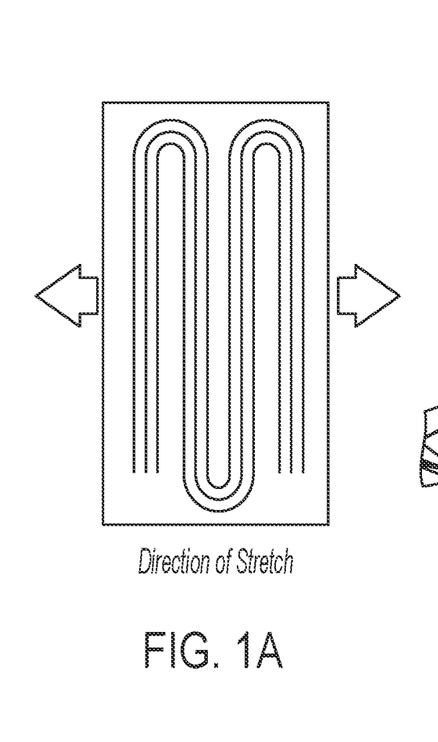
FIGS. 1A and 1B, is a depiction of an exemplary set of tubing (1A) and thermoregulatory apparel comprising such tubing (1B), according to at least one embodiment of the present invention.

Exemplary versions of the cooling vest, including the layout of the plurality of tubing, are shown in FIG. 1. In particular, FIG. 1A is an illustrated depiction of a sinusoidal layout (also referred to herein as a "serpentine" layout) of tubing. The term "sinusoidal layout" herein refers to a layout having the form of alternating peaks and valleys. It should be appreciated that such peaks and valleys need not be symmetric, regular, or periodic. The layout may also comprise a nested sinusoidal arrangement (e.g., in which the alternating peaks and valleys of certain portions of tubing are nested next to the alternating peaks and valleys of other portions of tubing). A skilled artisan will appreciate that this serpentine layout enables stretching of the cooling vest from side-to-side, that is, along the horizontal axis of the cooling vest, as depicted by the arrows in FIG. 1A. It will further be appreciated that such a stretch is important in enabling movement of a user that is wearing the cooling vest, as well as enabling the vest to fit properly on the torsos of users with different body sizes and shapes. This layout of the tubes eliminates possible constraints to breathing while the fabric conforms to the body.

Figure 1B:
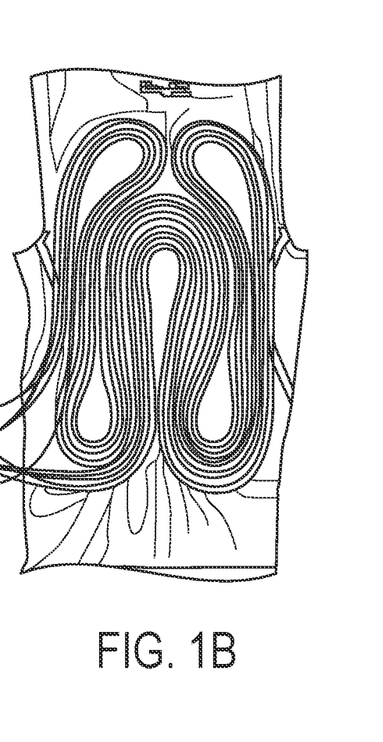

FIG. 1B illustrates an exemplary serpentine layout of the plurality of tubing overlaid on an exemplary 4-way stretch fabric, before the tubing and the fabric are combined to form the cooling vest. One of skill in the art will appreciate that both the tubing layout and the 4-way stretch fabric permit stretching in the horizontal direction (i.e., either to the left or to the right of the vest, as illustrated). It should further be appreciated that the fabric of the vest, as well as other wearable, thermoregulatory apparel comprising an embodiment of the present invention, can be designed and/or chosen based on human physiology and torso structure such that the fabric has the same or a similar amount of horizontal stretch as the serpentine layout of the plurality of tubing.

Figure 2A:
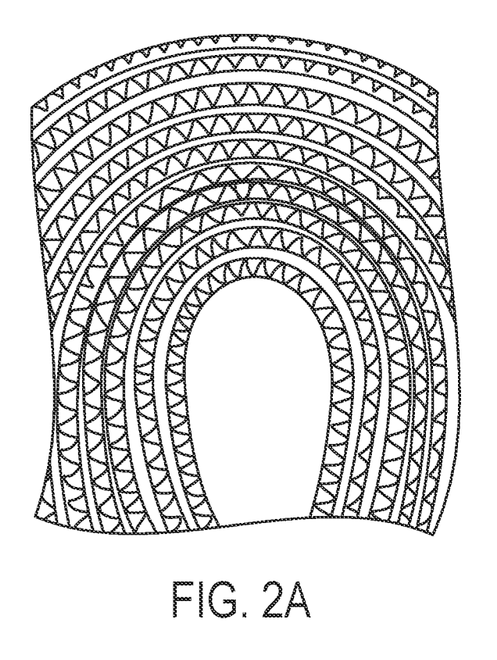
FIGS. 2A and 2B, depict of an exemplary stitching method for securing tubing to apparel fabric shown from the outside (2A) and inside (2B), according to at least one embodiment of the present invention.
Figure 2B:
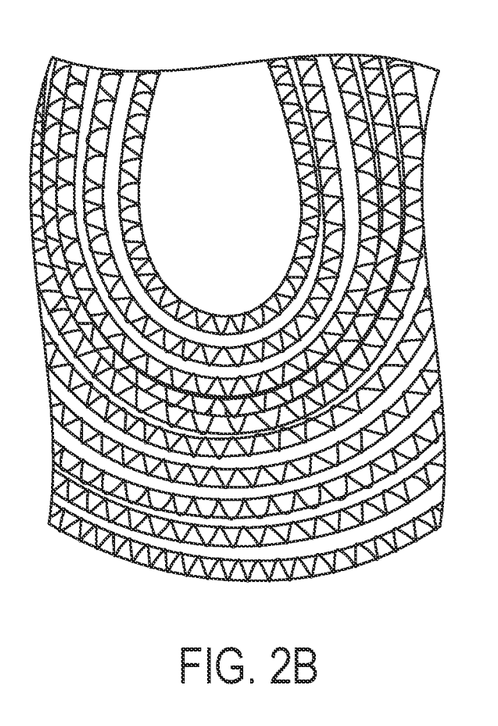

In one or more embodiments of the present invention, the plurality of tubing is sewn on the fabric used for the apparel using a modified cording foot, thereby allowing for the minimum bend radius of the tubing on the fabric. FIG. 2, and specifically FIGS. 2A and 2B, depict such a modified cording foot. This stitching pattern enables the elimination of snags and hazards, and further allows for spacing of the tubing that permits maximum thermoregulation, including, for example, maximum heat extraction from the surface of the user's body. Purely as a non-limiting example, the pitch between different sections of tubing in the plurality of tubing may be between 6.6 mm and 20 mm, and further may be 6.6 mm+1 mm. Generally, greater spacing increases efficiency of cooling (cooling/ft of tubing), while closer spacing increases maximum cooling at the loss of efficiency.

As stated above herein, it should be appreciated that the flexibility of the tubing is balanced with the stretch of the fabric. The stretching of the fabric increases contact between the plurality of tubing and the body of the user by flexing the tubes to fit the contours of the body. Therefore, tubing that is insufficiently flexible results in the fabric being pulled away from the body, thereby limiting the apparel's thermoregulatory capabilities, while tubing that is too flexible results in the flow of coolant being impeded. Purely metallic tubing is thus generally not useful for this application, while a range of polymer and rubber tubing demonstrate acceptable cooling characteristics when used in the system. Other types of tubing may also be used in the system, including, for instance, metal-infused tubing (e.g., tubing made with copper-infused elastomeric material), and elastic tubing.

While the use of modular cooling cartridges in conjunction with the cooling vest is described below, such a vest may also be used in conventional prior-art portable cooling systems, utilizing for example a portable vapor compression unit and battery.

Figure 3:
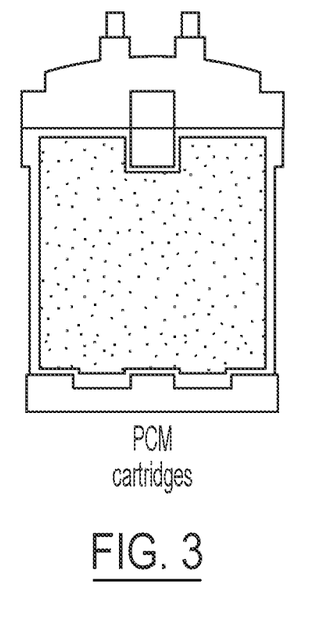
FIG. 3 is a depiction of an exemplary cartridge with a Phase Control Material (PCM), according to at least one embodiment of the present invention.

The cooling vest or other wearable, thermoregulatory apparel may further comprise one or more cartridges that each provides a capacity for controlling temperature in different conditions and in different use scenarios. An exemplary cartridge designed for cooling is shown in FIG. 3, which depicts a sealed container that contains a Phase Change Material (PCM). The cartridge will be described in more detail herein with particular reference to the one or more embodiments of the present invention that comprise a cooling vest or other cooling apparel. A skilled artisan will appreciate that the coolant circulating through the plurality of tubing will eventually have reduced or limited cooling ability, since the coolant absorbs heat generated by the user's body. Therefore, the coolant must be cooled and/or replaced such that the cooling ability of the coolant is renewed, thereby allowing the coolant to continue absorbing heat from the user. The cartridge generally enables such cooling and/or replacement of coolant.

In at least one embodiment of the invention, a wearable cooling system is described. This system comprises a wearable garment (e.g., a cooling vest) comprising a fabric portion and a first plurality of tubing secured to the fabric portion so as to contact a user's skin while the user is wearing the garment; at least one cartridge comprising a second plurality of tubing and a phase change material (PCM), wherein the PCM is configured to be in thermal contact with coolant passing through the second plurality of tubing; and one or more connectors for connecting the first plurality of tubing with the second plurality of tubing. The first and/or second plurality of tubing may be sewn into the fabric portion, as described above herein. Additional securing and/or attachment mechanisms are known in the art and include, for instance, adhesion via an adhesive, clips, pins, fasteners (e.g., hook-and-loop fasteners, hook-and-pile fasteners), and the like. Further, the fabric portion may have any of the stitching patterns described above herein, such as, for instance, a modified cording foot.

Figure 4:
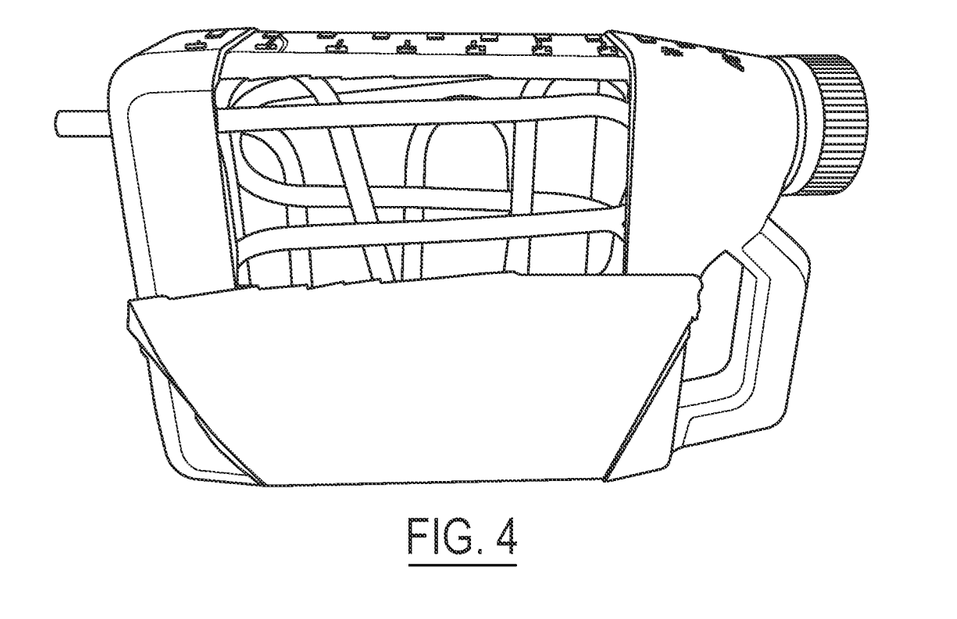
FIG. 4 is a depiction of a rudimentary cartridge, showing the internal tubing, according to at least one embodiment of the present invention.

The cartridge may comprise tubing (e.g., the second plurality of tubing) made of the same or a different material as the tubing in the vest (e.g., the first plurality of tubing), and may be configured so that the user may flow the coolant from the plurality of tubing in the vest into the tubing in the cartridge. FIG. 4 is a depiction of a rudimentary cartridge, showing the internal tubing. PCM would fill the remainder of the container surrounding the tubing.

As the coolant flows through the cartridge, the low-temperature PCM surrounding the tubing reduces the temperature of the coolant by absorbing heat from the coolant through the walls of the tubing via conduction, thereby renewing/increasing the coolant's cooling ability. After the coolant flows through the cartridge, and the cooling ability of the coolant is increased, the coolant may then be passed from the cartridge back into the plurality of tubing in the vest. The coolant may then recirculate through the vest until the temperature of the coolant needs to be reduced again.

In certain embodiments of the present invention, the coolant is either water or water mixed with up to 30% glycol by weight, such as 10% glycol, and the PCM is ice. Any known coolant may be utilized. Various known PCM materials may also be used, such as paraffins, salt hydrates, etc. PCM is useful for this application because as it changes phase from solid to liquid, the liquid maintains the same temperature until all the solid has changed phase. Thus, it offers a constant and predictable level of cooling for an extended period of time. Nevertheless, in some embodiments another material may be substituted for a PCM. For example, a fluid or solid material that does not undergo phase change in normal operating temperatures may be cooled to a low temperature and used instead of a PCM.

In some embodiments, the apparel may be used for heating a wearer instead of cooling. In such a case, the chosen PCM may change to solid state near and above human body temperature (e.g. ~110° F.).

It should be appreciated that a variety of different cartridges may be used with the cooling vest or other cooling apparel, depending on the user's needs and the desired temperature and duration of cooling. It should further be appreciated that the specific thermoregulatory properties of a given cartridge depends on the PCM contained within. That is, each cartridge may have a different cooling ability depending on a variety of factors, including, for example, a different PCM, a different volume for holding the PCM, and the like.

Figure 5:
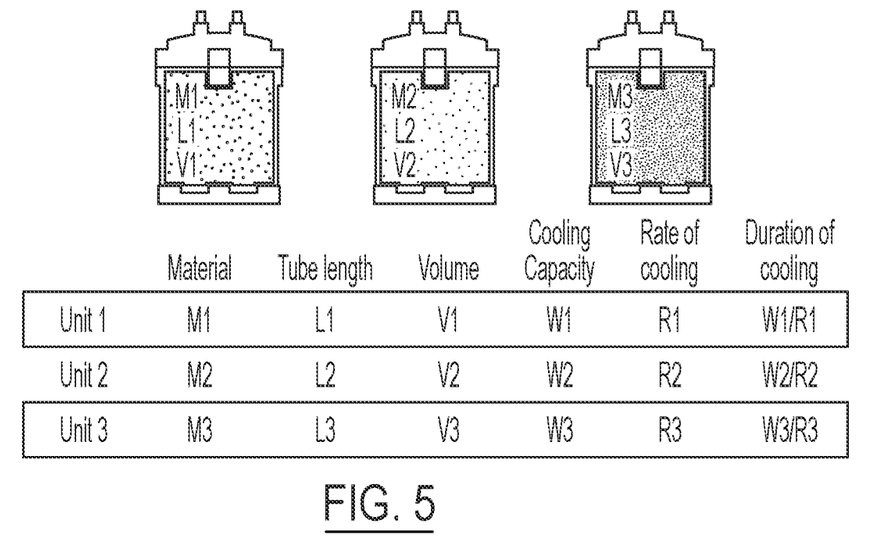
FIG. 5 is a depiction of three exemplary cartridges each with a different PCM, tube length, volume, cooling capacity, and rate of cooling, according to at least one embodiment of the present invention.

This variety of factors is shown with particular reference to FIG. 5, which depicts three exemplary cartridges (Units 1-3), each with a different PCM in the cartridge (M1-M3), a different length of tubing in the cartridge (L1-L3), a different cartridge volume (V1-V3), a different cooling capacity (W1-W3), and a different rate of cooling. Cooling capacity may be measured in Watts*minutes, while rate of cooling may be measured in Watts. As shown, the general formula for the duration of cooling is equal to the ratio of the cooling capacity (W1, W2, and W3) to the rate of cooling (R1, R2, and R3). Thus, the cooling duration of each of the three different cartridges depends on both the cooling capacity of each cartridge (which is affected, in part, by the type of PCM in each cartridge and cartridge (i.e. PCM) volume) and the rate of cooling (which, as described above herein, is affected, in part, by the amount of tubing associated with each cartridge). It should therefore be appreciated that a user may alter the amount of cooling he or she receives in the cooling vest by choosing a specific cartridge with a combination of factors that suits his or her needs. Purely as a non-limiting example, two cartridges with identical volume, but having two different lengths of tubing inside, can provide a different outlet temperature of the coolant, thereby leading to increased cooling.

It should further be appreciated that the operating range of any coolant used should be lower than the freezing temperatures of the material in the cartridge. This will allow the same coolant to be used across the entire system without requiring priming or introduction of air into the system. In at least one embodiment of the present invention, the coolant is circulated through the plurality of tubing in the cooling vest without the need for a power source, such as, for example, a battery pack. Instead, a pump is used to circulate coolant, including, for instance, a diaphragm pump, a peristaltic pump, and/or other similar pumps. A diaphragm pump, for example, has the advantage of not requiring priming. In at least one embodiment of the present invention, a manual or biomechanical pump is used to circulate the coolant in the system creating a passive system.

Figure 6:
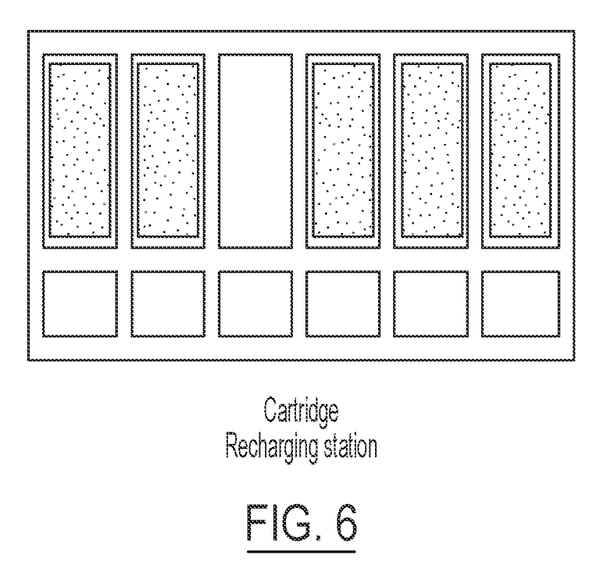
FIG. 6 is a depiction of an exemplary cartridge recharging station, according to at least one embodiment of the present invention.

Turning now to FIG. 6, an exemplary recharging system for one or more cartridges is shown. This system will be described in more detail with particular reference to the one or more embodiments of the invention that comprise cartridges that provide cooling. The recharging system may therefore be used to recharge the PCM within a cartridge once that PCM's ability to increase the cooling ability of coolant circulating through the cartridge tubing has diminished and/or ceased.

One of skill in the art will realize that the PCM will have its cooling ability diminish since it absorbs heat from the coolant when the PCM is recharging the coolant (i.e., increasing the cooling ability of the coolant) and may also absorb heat from the environment, although insulation of the cartridge may be utilized to reduce such heat loss. Thus, the PCM itself must eventually be recharged. The recharging system may be used to recharge one or more cartridges at a time by, for example, slotting the one or more depleted cartridges into the recharging system and running a coolant through the cartridges that is colder than the PCM currently inside the one or more depleted cartridges. This coolant may be the same as, or different from, the coolant used in the cooling vest. Purely as a non-limiting example, in an embodiment in which the coolant used in the cooling vest is water and 10% glycol and the PCM is ice, the cartridge recharging system may run that same coolant (water and 10% glycol) at a lower temperature than the ice currently in a depleted cartridge in order to recharge the PCM (i.e., reconstitute the ice from melt water in the cartridge, and eventually reduce the temperature of the ice in the cartridge below freezing).

It should be appreciated that, in at least one embodiment of the invention, the cartridge recharger described above herein may be part of a wearable cooling system that comprises both the recharger and a cooling vest or other wearable, thermoregulatory apparel. The cartridge recharger may be configured to replace the PCM and/or restore cooling capacity of the PCM. To restore cooling capacity, the cartridge recharger may, for example, be configured to connect to, and flow, coolant through the plurality of tubing located in the cartridge to reduce the temperature of the PCM, thereby restoring the PCM's cooling capacity. After the coolant restores the PCM's cooling capacity, it may flow back into the cartridge recharger to be stored for further use and/or flow into the plurality of tubing inside the cooling vest. It should be appreciated that, in at least one embodiment, the cartridge recharger is capable of simultaneously recharging or replacing the PCM in two or more cartridges.

It should be appreciated that at least one embodiment of the present invention permits high heat extraction from the body of the user through increasing body contact between the body and a cooling mechanism embedded in the apparel, such as, for example, the plurality of tubing. It should also be appreciated that one or more embodiments of the present invention balances the need to thermoregulate the user with the need for the user to retain maximum mobility while wearing the apparel. Therefore, the thermoregulation of the apparel is balanced against the need of the fabric to properly stretch, which requires, in part, adequate flexibility in the plurality of tubing to enable such stretch.

It should additionally be appreciated that the weight of the thermoregulatory apparel disclosed herein, including, for instance, the cooling vest disclosed herein, is lower than that of currently-available commercial alternatives. This weight reduction is due, in part, to the use of the cartridges described herein that provide temperature regulation. Current cooling vests utilize battery packs or other mobile sources of power to provide cooling, and must be worn by the user. Purely as a non-limiting example, embodiments of the present invention comprise cartridges that each weigh around 2 lb., while the backpacks associated with current commercial cooling vests weigh around 7-8 lb.

Additional weight reduction may be had by utilizing lighter tubing than what is currently used. For instance, the tubing used in the cooling vest may be made of a thermally conductive material that comprises one or more base polymers and one or more substances that increase the thermal conductivity of the one or more base polymers. These one or more substances may comprise one or more additives that can include, for example, metal or ceramic additives, such as, for instance, graphite fibers. The thermally conductive material may also comprise a secondary polymer and/or a plasticizer, either or both of which serve to reduce hardness of the thermally conductive material. The secondary polymer can include, for instance, ethylene propylene diene monomer (EPDM), and the plasticizer can include, for example, bis(2-ethylhexyl) adipate (DEHA). Most of the system's tubing is located outside the cartridge, in the vest/apparel portion. Since tubing within the cartridge need not be flexible, tubing material may vary between the cartridge and apparel portions. For example, tubing material in a cartridge may be copper or another metal to provide a high rate of heat transfer and reduce the chances of kinking or blocked flow.

These and other objectives and features of the invention are apparent in the disclosure, which includes the above and ongoing written specification and appended claims.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

I claim:

1. A wearable thermoregulatory apparel, the apparel comprising:
    a four-way stretch fabric formed into a garment; and
    a plurality of tubing secured to the four-way stretch fabric such that heat may be exchanged by conduction between the plurality of tubing and a user's skin while the user is wearing the garment,
    wherein the plurality of tubing comprises one or more serpentine arrangements, and
    wherein the one or more serpentine arrangements comprises a nested sinusoidal arrangement.

2. The apparel of claim 1, wherein the plurality of tubing has a pitch of between 6.6 mm and 20 mm.

3. The apparel of claim 1, wherein the plurality of tubing is configured to allow a liquid to flow through the plurality of tubing while the user is wearing the garment.

4. The apparel of claim 3, wherein the liquid comprises a substance that lowers a freezing point of the liquid.

5. The apparel of claim 4, wherein the liquid is water and the substance is glycol.

6. The apparel of claim 5, wherein the glycol is up to 30% by weight of the water-glycol mixture.

7. The apparel of claim 6, wherein the glycol is 10% by weight of the water-glycol mixture.

8. The apparel of claim 1, wherein the plurality of tubing is sewn into the four-way stretch fabric using a modified cording foot pattern.

9. The apparel of claim 1, wherein the nested sinusoidal arrangement comprises a plurality of curved sections of the plurality of tubing, the plurality of curved sections comprising a first curved section and a second curved section, and wherein the first curved section is disposed adjacent to the second curved section.

10. The apparel of claim 9, wherein the plurality of curved sections is further arranged such that breathing of a user is not constrained when wearing the garment.

11. The apparel of claim 9, wherein a pitch between the first curved section and the second curved section is 6.6 mm to 20 mm.

12. A wearable cooling system, the system comprising:
    a wearable garment comprising a fabric portion and a first plurality of tubing secured to the fabric portion so as to contact a user's skin while the user is wearing the garment;
    at least one cartridge comprising a second plurality of tubing and a phase change material, wherein the phase change material is configured to be in thermal contact with a coolant passing through the second plurality of tubing; and
    one or more connectors for connecting the first plurality of tubing with the second plurality of tubing,
    wherein the first plurality of tubing is composed of a thermally conductive material,
    wherein the first plurality of tubing comprises one or more serpentine arrangements, and
    wherein the one or more serpentine arrangements comprises a nested sinusoidal arrangement.

13. The cooling system of claim 12, further comprising the coolant configured to cool the user by conduction through the first plurality of tubing.

14. The cooling system of claim 13, wherein the coolant is water with up to 30% by weight glycol.

15. The cooling system of claim 12, further comprising a cartridge recharger configured to replace the phase change material or restore cooling capacity of the phase change material.

16. The cooling system of claim 15, wherein the cartridge recharger is configured to connect to and flow the coolant through the second plurality of tubing to reduce a temperature of the phase change material and thereby restore the cooling capacity of the phase change material.

17. The cooling system of claim 15, wherein the at least one cartridge comprises two or more cartridges, and wherein the cartridge recharger is capable of simultaneously recharging or replacing the phase change material in each of the two or more cartridges.

18. The cooling system of claim 12, wherein the first plurality of tubing and the second plurality of tubing are made from identical materials.

19. The cooling system of claim 12, wherein the at least one cartridge comprises two or more cartridges, and wherein:
    the phase change material in each of the two or more cartridges is different,
    the second plurality of tubing has a different length in each of the two or more cartridges, and/or
    the phase change material has a different volume in each of the two or more cartridges.

20. The cooling system of claim 12, wherein the thermally conductive material comprises one or more base polymers and one or more additives that increase a thermal conductivity of the one or more base polymers.

21. The cooling system of claim 20, wherein the one or more additives comprise graphite fibers.

22. A method for thermoregulation of a user using a wearable apparel, the method comprising:
    wearing a garment comprising a four-way stretch fabric and a first plurality of tubing secured to the four-way stretch fabric so as to contact a user's skin while the user is wearing the garment;
    flowing a coolant through the first plurality of tubing;
    connecting at least a portion of the first plurality of tubing to a second plurality of tubing in a cartridge, wherein the cartridge comprises a phase change material; and
    passing the coolant through the phase change material in the cartridge and back to the first plurality of tubing,
    wherein the first plurality of tubing comprises one or more base polymers and one or more additives that increase a thermal conductivity of the one or more base polymers,
    wherein the first plurality of tubing comprises one or more serpentine arrangements, and
    wherein the one or more serpentine arrangements comprises a nested sinusoidal arrangement.

23. The method of claim 22, further comprising:
    placing the cartridge in a cartridge recharger; and
    utilizing the cartridge recharger to recharge or replace the phase change material in the cartridge.

24. The method of claim 23, wherein the utilizing step comprises:
flowing a fluid through the second plurality of tubing; and
reducing the phase change material's temperature.

25. The method of claim 22, wherein the flowing step is performed by a source that does not require priming.

26. The method of claim 22, wherein the first plurality of tubing comprises a secondary polymer and/or a plasticizer.

27. The method of claim 22, wherein the secondary polymer comprises ethylene propylene diene monomer (EPDM).

28. The method of claim 22, wherein the plasticizer comprises bis(2-ethylhexyl) adipate (DEHA).

* * * * *